(12) United States Patent
Dross et al.

(10) Patent No.: US 10,689,655 B2
(45) Date of Patent: Jun. 23, 2020

(54) OFF-AXIS COLLIMATION OPTICS

(71) Applicant: Light Prescriptions Innovators, LLC, Altadena, CA (US)

(72) Inventors: Oliver Dross, Cologne (DE); Fernando Munoz, Madrid (ES)

(73) Assignee: Seoul Semiconductor Co., Ltd., Ansan (KR)

( * ) Notice: Subject to any disclaimer, the term of this patent is extended or adjusted under 35 U.S.C. 154(b) by 104 days.

(21) Appl. No.: 15/843,685

(22) Filed: Dec. 15, 2017

(65) Prior Publication Data

US 2018/0112227 A1 Apr. 26, 2018

Related U.S. Application Data

(62) Division of application No. 13/574,016, filed as application No. PCT/US2011/022067 on Jan. 21, 2011, now Pat. No. 9,885,458.

(Continued)

(51) Int. Cl.
| | |
|---|---|
| *C12N 15/70* | (2006.01) |
| *F21V 7/00* | (2006.01) |
| *G02B 17/08* | (2006.01) |
| *F21V 5/08* | (2006.01) |
| *G02B 19/00* | (2006.01) |
| *F21V 5/04* | (2006.01) |
| *C07K 14/005* | (2006.01) |
| *H01L 33/58* | (2010.01) |

(Continued)

(52) U.S. Cl.
CPC ............ *C12N 15/70* (2013.01); *C07K 14/005* (2013.01); *F21V 5/04* (2013.01); *F21V 5/08* (2013.01); *F21V 7/0091* (2013.01); *G02B 17/086* (2013.01); *G02B 19/0028* (2013.01); *G02B 19/0061* (2013.01); *C07K 2319/21* (2013.01); *C07K 2319/23* (2013.01); *C12N 2750/10022* (2013.01); *C12N 2800/22* (2013.01); *F21W 2131/103* (2013.01); *F21Y 2115/10* (2016.08); *H01L 33/58* (2013.01)

(58) Field of Classification Search
CPC .............. C07K 14/005; C07K 2319/21; C07K 2319/23; C12N 15/70; C12N 2750/10022; C12N 2800/22; F21V 5/04; F21V 5/08; F21V 7/0091; F21W 2131/103; F21Y 2115/10; G02B 17/086; G02B 19/0028; G02B 19/0061; H01L 33/58
See application file for complete search history.

(56) References Cited

U.S. PATENT DOCUMENTS

| | | |
|---|---|---|
| 2,215,900 A | 9/1940 | Bitner |
| 5,757,557 A | 5/1998 | Medvedev et al. |

(Continued)

FOREIGN PATENT DOCUMENTS

| | | |
|---|---|---|
| WO | 0024062 A1 | 4/2000 |

*Primary Examiner* — Joseph P Martinez
*Assistant Examiner* — Vipin Patel
(74) *Attorney, Agent, or Firm* — Faegre Drinker Biddle & Reath LLP

(57) ABSTRACT

A light funnel collimator has a central lens surface and a back reflecting surface, shaped to provide a wider background beam and a narrower hotspot beam within but off-center of the wider beam. One of the beams is on-axis of the collimator, and the other beam is off-axis. The reflector is at least partly asymmetrical relative to the axis, and provides or contributes to the off-axis beam.

12 Claims, 8 Drawing Sheets

Related U.S. Application Data

(60) Provisional application No. 61/298,030, filed on Jan. 25, 2010.

(51) Int. Cl.
*F21Y 115/10* (2016.01)
*F21W 131/103* (2006.01)

(56) References Cited

U.S. PATENT DOCUMENTS

| | | |
|---|---|---|
| 6,924,943 B2 | 8/2005 | Minano et al. |
| 8,388,193 B2 | 3/2013 | Wilcox et al. |
| 8,465,180 B2 | 6/2013 | Van Oers et al. |
| 2002/0080615 A1 | 6/2002 | Marshall et al. |
| 2004/0070855 A1 | 4/2004 | Benitez et al. |
| 2007/0086204 A1 | 4/2007 | Chinniah et al. |
| 2009/0128921 A1 | 5/2009 | Roth |
| 2009/0154185 A1* | 6/2009 | Yagi .................... F21V 5/08 362/516 |
| 2012/0287511 A1* | 11/2012 | Dross .................... F21V 5/04 359/641 |

* cited by examiner

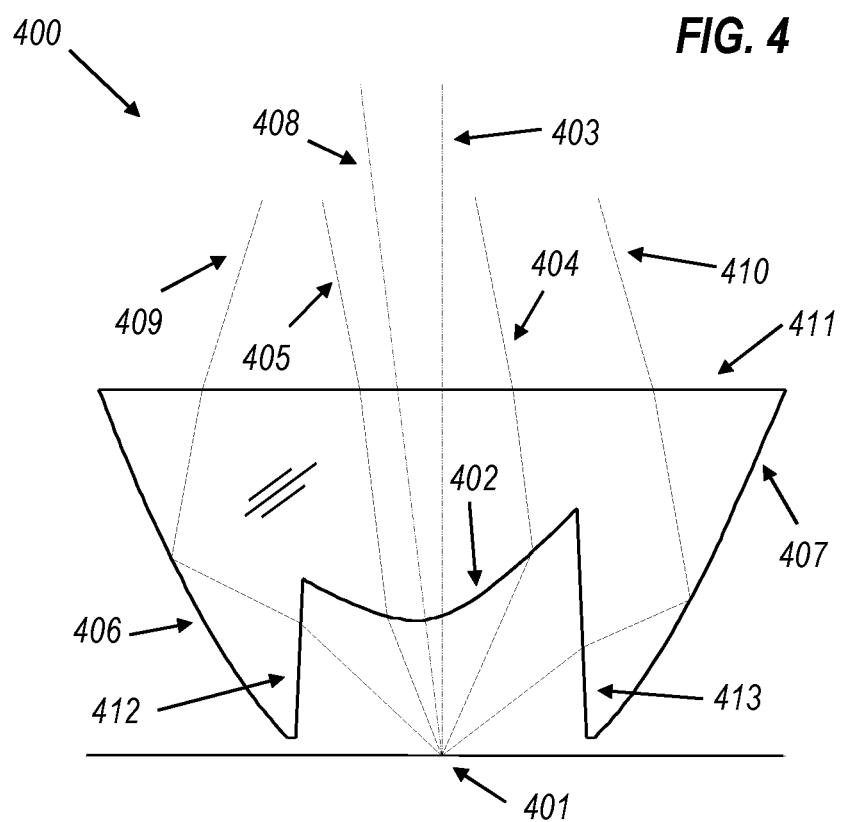

OFF-AXIS COLLIMATION OPTICS

CROSS REFERENCE TO RELATED APPLICATIONS

This application is a divisional of U.S. patent application Ser. No. 13/547,016, which is a national stage of PCT/US2011/022067, filed on 21 Jan. 2011 and published as WO 2011/091259 on 28 Jul. 2011, the entire content of which is incorporated herein by reference, and which claims benefit of U.S. Provisional Patent Application No. 61/298,030, filed Jan. 25, 2010. All of those applications are by Dross et al. for "Off-axis collimation optics."

BACKGROUND OF THE INVENTION

Light emitting diodes (LEDs) are widely available, inexpensive, and efficient light sources. For uses such as sport headlamps, one or two state of the art LEDs provide adequate light. While simple light distributions of rotational symmetry are sufficient for low quality products or less demanding uses, more complex light distributions are being employed for better vision when walking, running, or cycling with a headlamp. It is beneficial to produce a relatively narrow hotspot of typically 10° full width at half maximum (FHWM) so to illuminate objects far away from the user, while a lower level intensity background light is needed to provide lighting of the ground close to the user. Such a background light is not needed upwards from the hotspot so that a background beam that is tilted relative to the hotspot beam is beneficial.

A collimator configuration as seen in FIG. 1 is used in a current headlamp product made by Silva Sweden AB that produces a wide beam off-axis background light around a narrow intense on-axis hotspot. The lens 100 is of a type herein called a "photon funnel" that has a central "collimator cavity" containing the light source. The wall of the cavity has a front or center lens 103 and a side or peripheral cavity surface. In a center section of the photon funnel, light passes by refraction through the center lens 103 and an exit surface (which in FIG. 1 is part of a front surface 104), while the majority of the light passes through the cavity side surface by refraction, is reflected by total internal reflection (TIR) at a back surface 102, and exits through the front surface 104 by refraction.

In the Silva product, the center lens 103 of lens 100 is a rotationally symmetric surface that has its rotational axis tilted with respect to the light source axis to provide an off-axis background light while surface 102 collimates the majority of the light from the LED to form a narrow hot spot. This architecture works well, if the amount of light that is needed for the background illumination is roughly one third of the full light emitted by a Lambertian LED, as this is the typical amount of light collected by the center lens of a conventional photon funnel. If more or less light is wanted in the off-axis beam, this configuration cannot be used. Moreover the center lens provides a relatively wide beam by nature of the lens 103, so that if a narrow off-axis beam is wanted, the center lens cannot provide such beam.

In all of the described embodiments, the cavity side surface is a surface of rotation about a center axis, and the light source is an LED chip centered on and coaxial with the center axis of the cavity. A typical LED chip is flat, and is a Lambertian emitter with its emission symmetrical about an axis perpendicular to the flat chip. The LED chip thus typically has a well-defined central axis. In the present specification, the terms "on-axis" and "off-axis" are used here with respect to the common center axis of the collimator cavity and the LED chip. In all of the embodiments, one of the hotspot beam and the background beam is directed along the center axis, and the other beam is directed along a second axis, referred to as a "tilted axis," diverging from the center axis. In all of the embodiments, the exit surface of the optics is flat, and the surface normal of the exit surface coincides with the cavity center axis. However, exit surfaces of other shapes and orientations can be implemented.

The head lamp itself often provides means to adjust the direction of light emission of the entire lamp, so that the narrow beam can be adjusted for far vision while the wide beam will provide near vision. Thus, as will be shown below with reference to FIG. 4, the same functionality as in the Silva lamp can be achieved by the "dual" case in which a tilted center lens provides a hotspot beam along the tilted axis, and an on-axis reflector provides an on-axis background beam. However, the simple dual configuration will then typically direct two-thirds of the light into the background beam and one-third into the hotspot beam, which may not be optimal.

Other applications besides sport headlamps of partially or fully off-axis LED collimators would be in architectural lighting to create certain lighting effects, such as illuminating a wall from a lighting fixture that is oriented parallel to the wall, in street lighting, and many other applications.

SUMMARY OF THE INVENTION

The optical approach explained in detail below does not rely solely on the center lens of a photon funnel to provide off-axis illumination. Using the TIR reflective back surface of a photon funnel for off-axis illumination has several advantages, among them: that much more flux impinges upon this surface; and that by the nature of reflection, modifications of the back surface make much larger off-axis beam tilt angle possible than with a single refraction at the center lens. In all of the embodiments described below, the optical designs are modified rotational designs. The rotational designs are obtained with common methods, either with point source approximation numerical or analytic methods or with extended source optimization using common iterative numerical methods. The starting point design can be a narrow-beam on-axis collimator, or part of the surfaces can be calculated to provide a wider on-axis beam. In a subsequent step some optical surfaces are modified to deviate from the rotational symmetry. All other surfaces may be left unchanged, including the so-called cavity surfaces (the circumferential wall of the central cavity, through which light enters the photon funnel dielectric on a path towards the back reflective surface) and the front (exit-) surface of the dielectric. In the following detailed description and drawings, examples of photon funnels with a fully or partially modified TIR back surface are described and shown. The center lens may or may not also be modified, to provide additional on and off axis illumination, and all combinations of modified center lenses and modified mirrors are possible. The back surface may be modified so that a modified section of the reflector surface provides off-axis light while an unmodified section provides on-axis light. Both beam spreads, the angle of tilt between the on and off-axis portions and their intensity patterns and levels can be controlled. When modifying both the center lens and back surface completely, all light can be sent off-axis, either in a single beam or in two (or more) differently tilted beams.

BRIEF DESCRIPTION OF THE DRAWINGS

The above and other aspects, features and advantages of the present invention will be apparent from the following more particular description thereof, presented in conjunction with the following drawings wherein:

FIG. 4 shows a photon funnel that provides a narrow off-axis hotspot from the center lens and a wide on-axis background illumination from the back surface.

FIG. 11 B shows the 3D wavefronts from the source and target used to derive the freeform back surface.

DETAILED DESCRIPTION OF THE PREFERRED EMBODIMENTS

A better understanding of the features and advantages of the present invention will be obtained by reference to the following detailed description of the invention and accompanying drawings, which set forth illustrative embodiments in which the principles of the invention are utilized.

Figure 1:
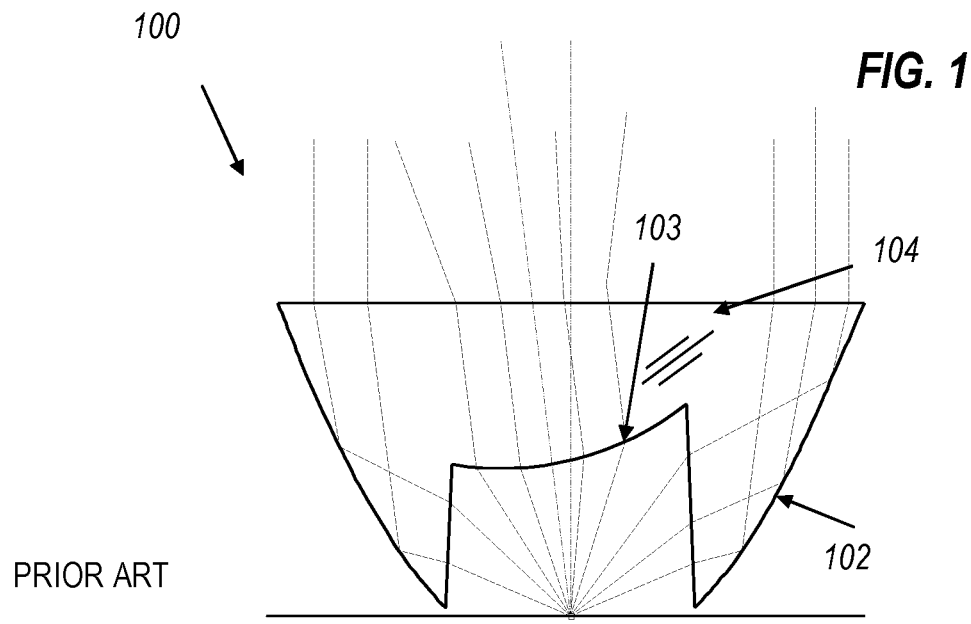
FIG. 1 shows a photon funnel of the prior art.
Figure 2:
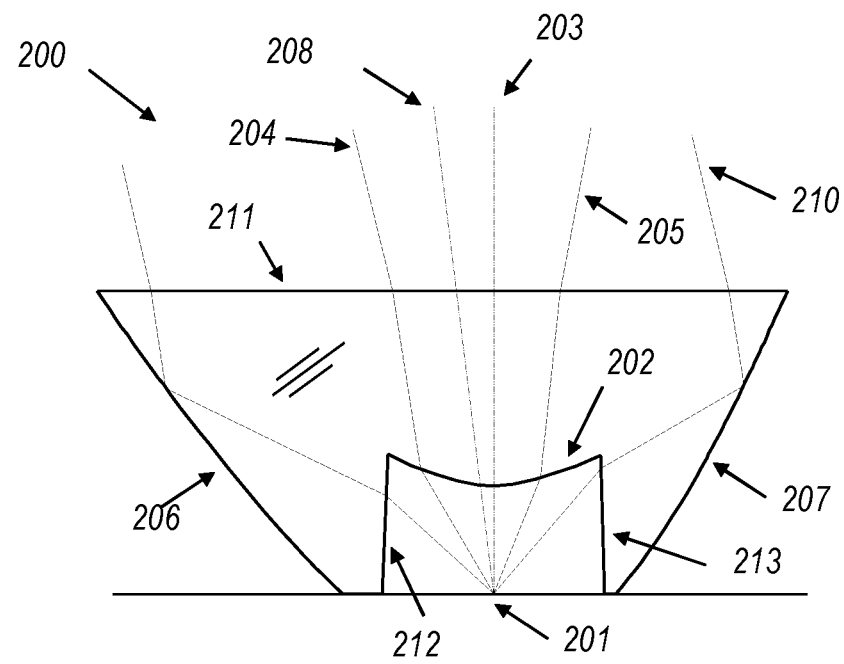
FIG. 2 shows the first preferred embodiment of a photon funnel with a back surface to provide off-axis narrow beam illumination and on-axis wide background light provided by the center lens.

In the following drawings all architectures are described in more detail:

Referring to FIG. 2, a lens 200 represents a photon funnel that collimates the light from a source 201 into an off-axis hot spot and also creates a low-intensity background illumination. The photon funnel 200 comprises a dielectric lens with a central cavity. Lines 212 and 213 in FIG. 2 are cross sections of a conical surface of rotation with respect to the source axis 203, forming the side wall of the cavity. Surface 202 forms a central lens, closing off the front end of the cavity, and is a rotationally symmetric surface around axis 203. Lens surface 202 is shaped so that rays such as 204 and 205 that are refracted at lens surface 202 and at flat exit surface 211 produce a uniform background illumination.

In general, references to a "surface of rotation," "rotationally symmetric surface," or similar indicate that the surface can be generated by rotation of a generator line, which may be straight, curved, or of a more complicated shape, about an axis, but do not require that the physical surface forms a complete annulus about the axis, nor that the axial ends of the physical surface form circles coaxial with the axis. As will be explained below, many of the embodiments described can be formed with surfaces that may be either a single annulus or two or more distinct arcs, and in many of the embodiments an axial boundary may be a junction (with or without an optically inactive step) between surfaces that are rotationally symmetric about different axes.

The back of photon funnel 200 is formed by a single continuous surface, represented by curves 206 and 207 in FIG. 2, that is rotationally symmetric with respect to an axis 208 that is tilted relative to the source axis 203. Thus, the curves 206, 207 are not identical, because they represent different parts of the surface of rotation, with curve 207 starting closer to the (tilted) axis 208. Reflective surface 206 is shaped so that rays such as 209 and 210 that are refracted at side surface 212 undergo total internal reflection at surface 206 and then exit through surface 211, forming an off-axis narrow beam pattern.

Figure 3A:
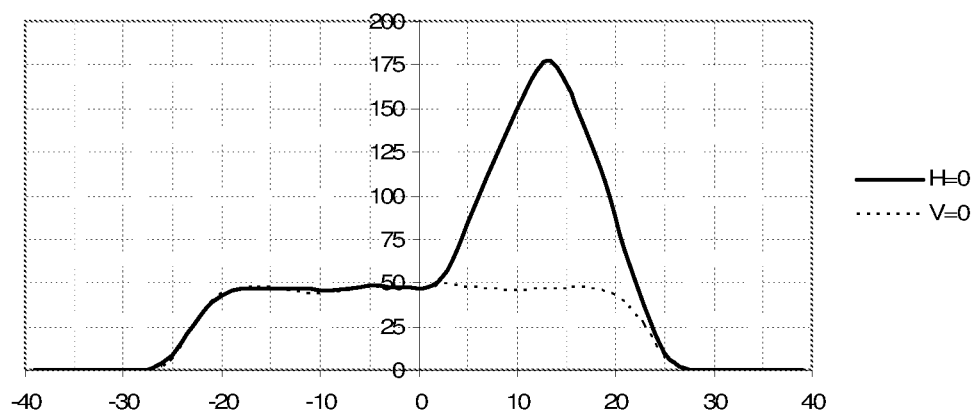
FIG. 3A shows an intensity distribution in the horizontal and vertical direction, of a photon funnel with an off-axis hotspot and an on-axis low intensity background intensity.
Figure 3B:
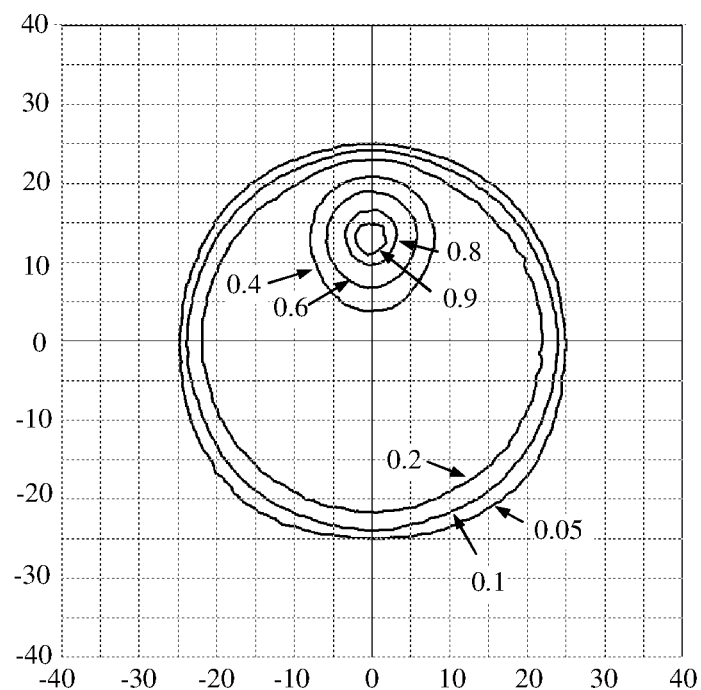
FIG. 3B shows the same radiation pattern as a 2 dimensional distribution.

FIG. 3A shows two-dimensional horizontal and vertical sections through a typical intensity pattern produced by a partially off-axis collimator such as that shown in FIG. 2. The background emitted by the center lens is located with its center on-axis. The light has a FWHM of about 45 deg. The hotspot, emitted by the back surface 206, is located off-axis. In FIG. 3B, a two-dimensional intensity pattern is shown to illustrate the same radiation pattern. The scales on the horizontal axis in FIG. 3A and the vertical and horizontal axes in FIG. 3B represent angles in degrees from the center axis 203. The contour lines in FIG. 3B and the vertical axis in FIG. 3A are normalized intensity levels.

Lens 400 in FIG. 4 is an optical device that collimates the light from a source 401 into an off-axis narrow hot spot and also creates a low-intensity background of rotational symmetry. A central cavity is bounded by a conical surface of rotation with respect to the source axis 403, seen in cross section as lines 412 and 413. Lens surface 402 is a rotationally symmetric surface around tilted axis 408. As a result, the line where lens surface 402 meets conical surface 412, 413 is tilted, shown by the greater length of section line 413 than section line 412. Rays such as 404 and 405 that are refracted at lens surface 402 and planar exit surface 411 will form the narrow off-axis beam pattern. Surface 406 forming the back of the light funnel 400 is rotationally symmetric around (non-tilted) light-source axis 403. The cross-section of surface 406 is calculated to provide a wide background pattern. Rays such as 409 and 410 that are refracted at surface 412, 413 undergo total internal reflection at the back surface, represented by curves 406 and 407, and then exit through planar surface 411.

Figure 5:
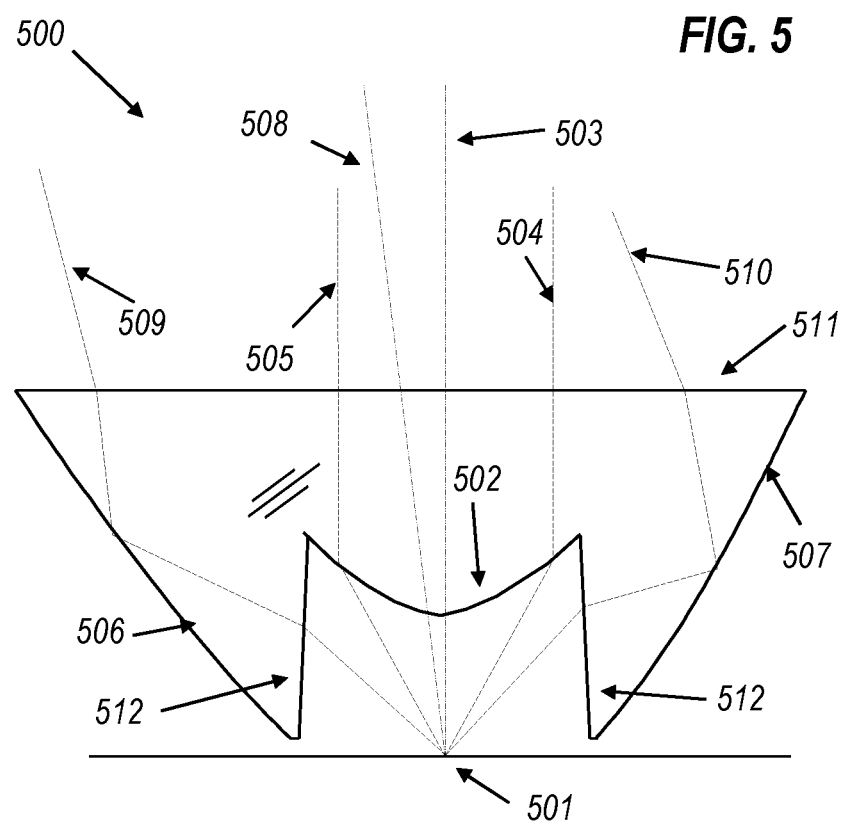
FIG. 5 shows a photon funnel that provides a narrow on-axis hotspot from the center lens and a wide off-axis background illumination from the back surface.

Lens 500 in FIG. 5 is an optical device that collimates the light from source 501 into an on-axis hot spot and also creates a low-intensity off-axis background illumination. A central cavity is bounded by conical surface 512, which is a surface of rotation with respect to the source axis 503, and by lens surface 502, which is a rotationally symmetric surface around source axis 503. Rays such as 504 and 505 that are refracted at lens surface 502 and planar exit surface 511 will form the narrow on-axis beam pattern. The back surface, represented by curves 506 and 507, is a rotationally symmetric surface around tilted axis 508. The cross-section of surface 506, 507 is calculated to provide an off-axis wide background pattern. Rays such as 509 and 510 that are refracted at conical surface 512 undergo total internal reflection at surface 506, 507 and then exit through planar surface 511.

Figure 6:
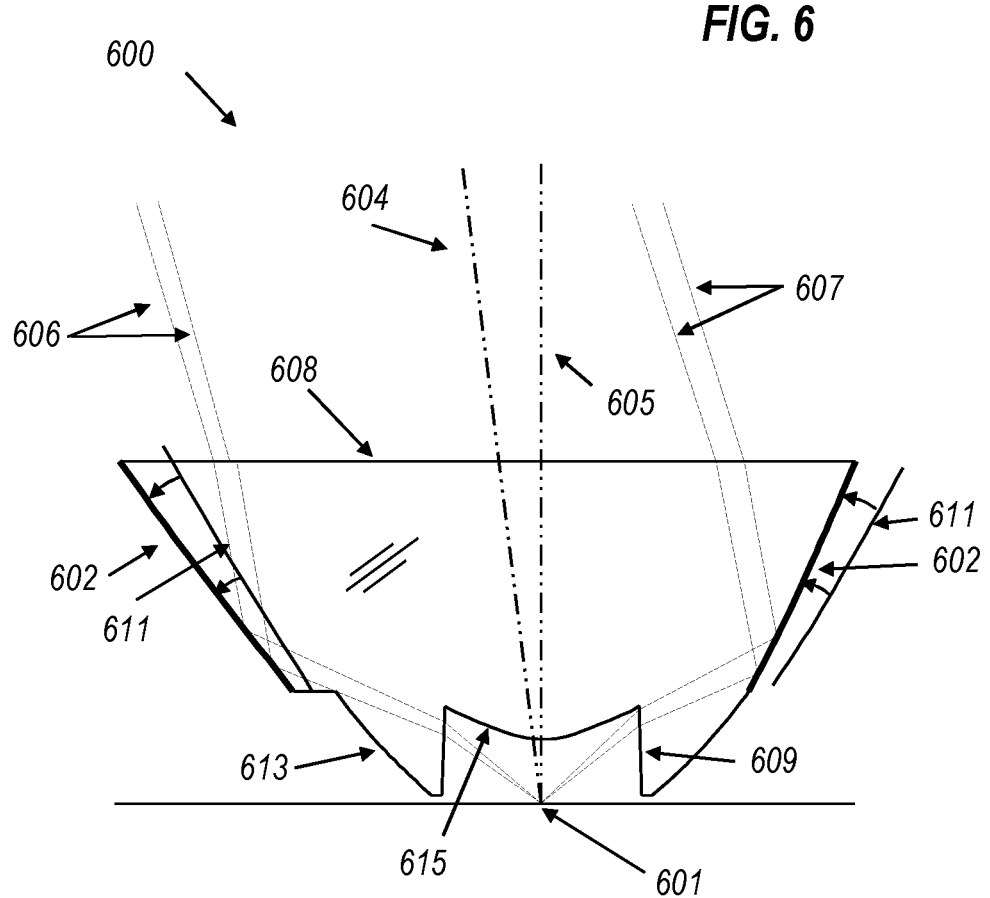
FIG. 6 shows a photon funnel that provides a narrow off-axis hotspot from a top section of the back surface.
Figure 7:
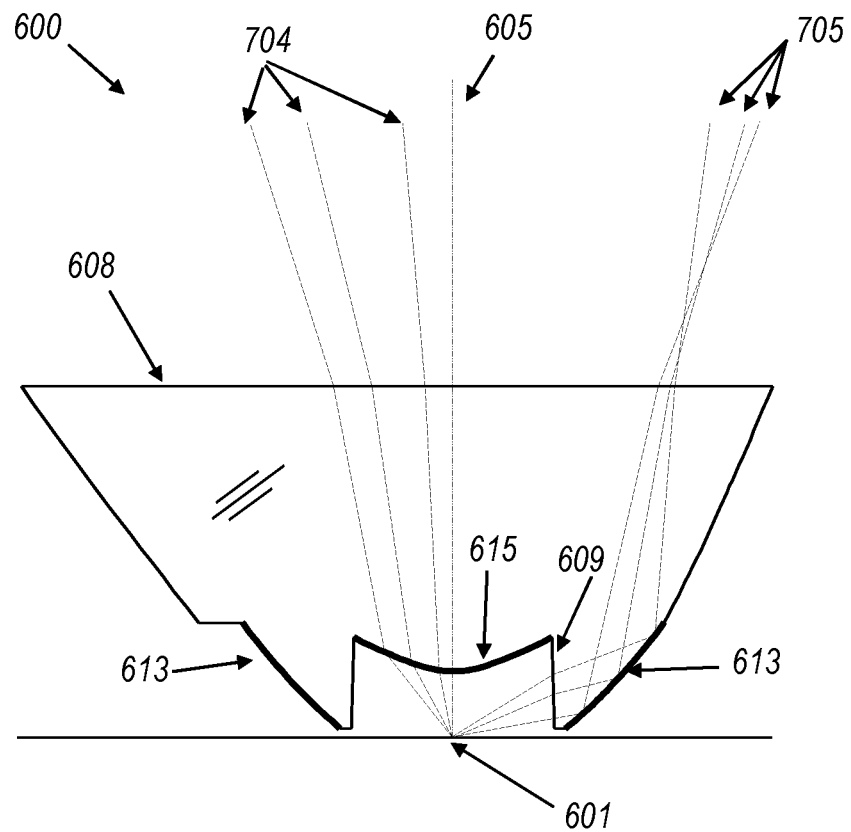
FIG. 7 shows a photon funnel that provides wide beam on-axis background illumination from a bottom section of the back surface.

Lens 600 in FIGS. 6 and 7 is an optical device that collimates the light from source 601 into an off-axis hot spot and also creates an on-axis low-intensity background. By splitting the back surface into sections, the amount of light directed into on-axis and off-axis beams can be adjusted to the application. Side surface 609 of the central cavity is a conical surface of rotation with respect to the source axis 605. Surface 602, which forms the front part of the TIR back surface of light funnel 600, is rotationally symmetric around tilted axis 604. Tilted reflector surface 602 may be seen as being obtained by tilting a surface 611 that is rotationally symmetric around source axis 605 around the center of source 601. Rays such as 606 and 607 that are refracted at cavity side surface 609, then undergo total internal reflection at tilted reflective surface 602, and then exit passing through flat front surface 608 will form the off-axis hot spot.

Lens surface 615 and reflective surface 613, which forms the rear part of the TIR back surface of light funnel 600, is rotationally symmetric around source axis 605. Rays 705 (see FIG. 7) that are refracted at cavity side surface 609, then undergo total internal reflection at on-axis reflective surface 613, and then exit passing through flat front surface 608 contribute to the on-axis background illumination. Rays 704 that are refracted at the front lens surface 615 of the cavity and then at the flat front surface 608 also contribute to the on-axis background illumination.

As may be seen from FIGS. 6 and 7, the relative intensities of the hot-spot and background beams may easily be set by choosing the position of the transition between the front and rear sections 602 and 613 of the reflector surface.

Figure 8:
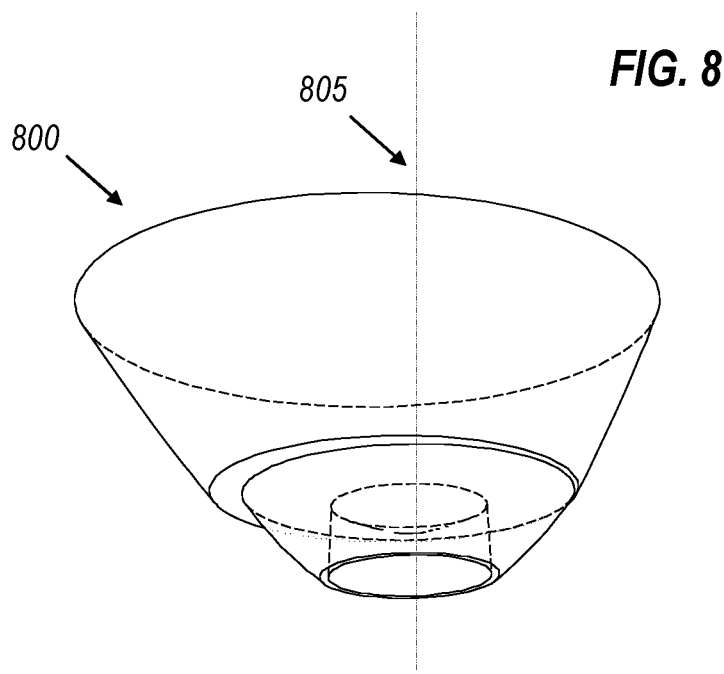
FIG. 8 shows a three dimensional view of a photon funnel as constructed according to FIG. 6 and/or FIG. 7.

FIG. 8 provides a three dimensional view of a photon funnel lens 800, with source axis 805, which may be similar to the lens 600 shown in FIGS. 6 and 7 described above.

Various methods of construction can be used to obtain a back surface of a photon funnel to provide off-axis illumination or non rotationally symmetric illumination:

1. The whole or a section of a rotationally symmetrical collimating back surface such as surface 611 is tilted (FIG. 6) around the source center by an angle equal to ArcSin((Sin θ)/n), where θ is the desired off-axis angle of the center of the illumination pattern and n is the index of refraction of the dielectric used. Because of the refraction of the light at the cavity wall 609, the system does not behave like a light source in an air filled reflector, so that for large pitch angles around the source center no optically "correct" surface for the illumination task can be obtained. For small angles of pattern center shift (up to approximately 20 deg) this method works sufficiently well. This solution provides an asymmetric exit aperture that is off centered from the optical axis 605.

Figure 9:
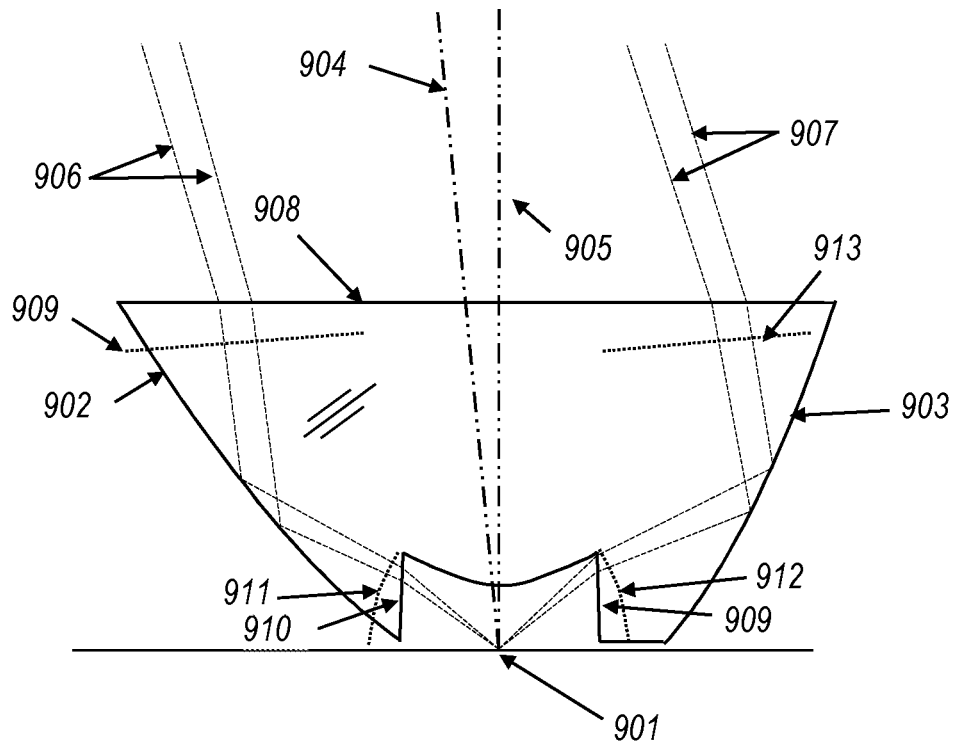
FIG. 9 shows the 2D wavefront method to calculate meridian cross-sections for an improved embodiment for off-axis illumination from the back surface.
Figure 10:
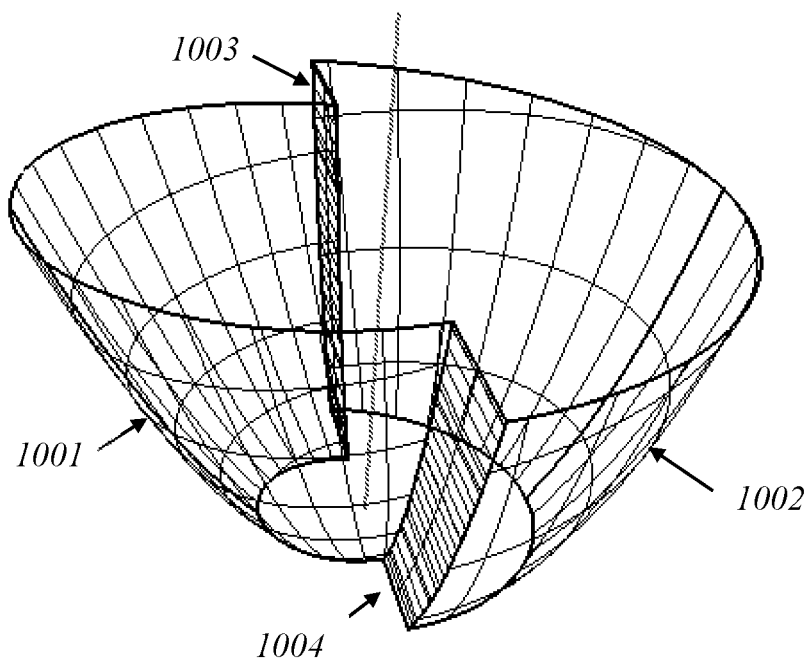
FIG. 10 shows a three dimensional view of the back surface constructed according to FIG. 9.

2. In FIG. 9 a more precise procedure is illustrated. A meridian cross-section 902 is calculated as a generalized Cartesian oval derived from off-axis wavefront 909 (outgoing wavefront after refraction at the exit surface 908) and source wavefront 911 (source wavefront after refraction at cavity wall 910). The source is treated like a point source, so that wavefront 911 can be represented as a spherical wavefront. The meridian cross-section 903 is calculated similarly from wavefronts 912 and 913. Both cross-sections are rotated around a tilted axis 904 and result in surfaces 1001 and 1002 in FIG. 10. In FIG. 10, only the back surfaces of the photon funnel are shown. The surfaces 1001 and 1002 do not necessarily intersect. The left half (as seen in FIGS. 9 and 10) of 1001 and the right half of 1002 are cut and connected by optically inactive surfaces 1003 and 1004.

Figure 11:
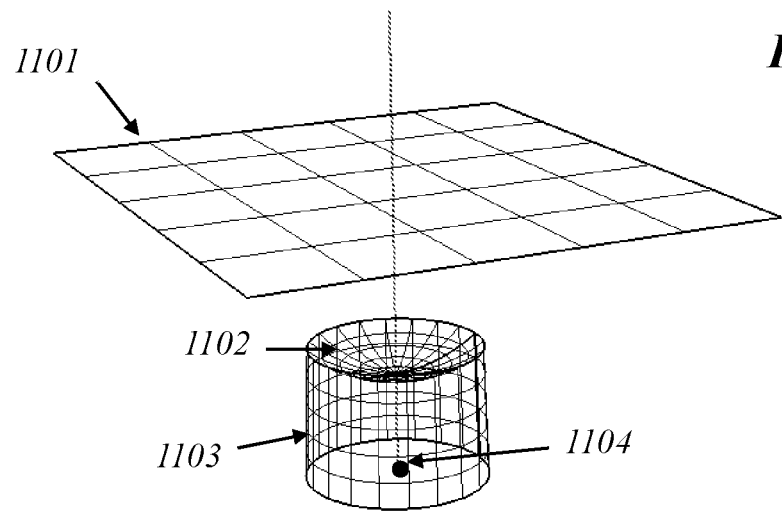
FIG. 11 A shows prefixed photon funnel surfaces from a standard rotational design.
Figure 11:
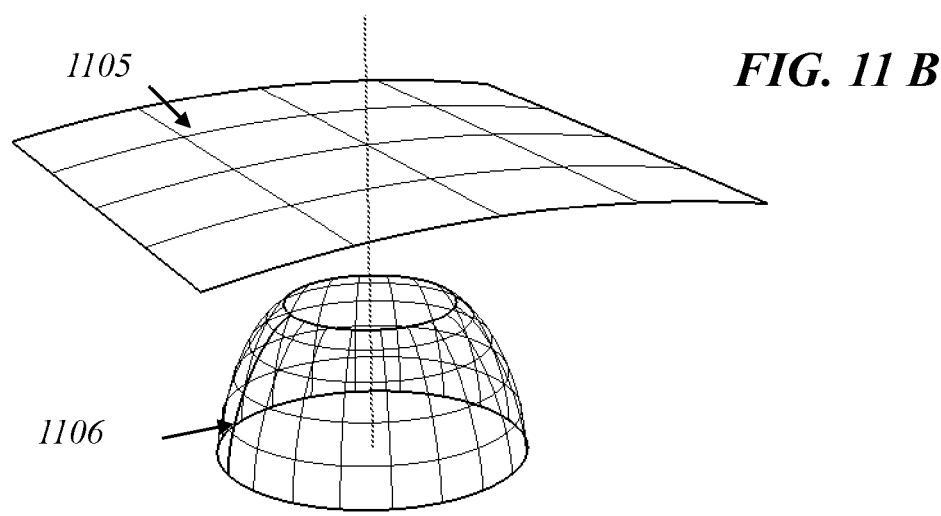
Figure 11:
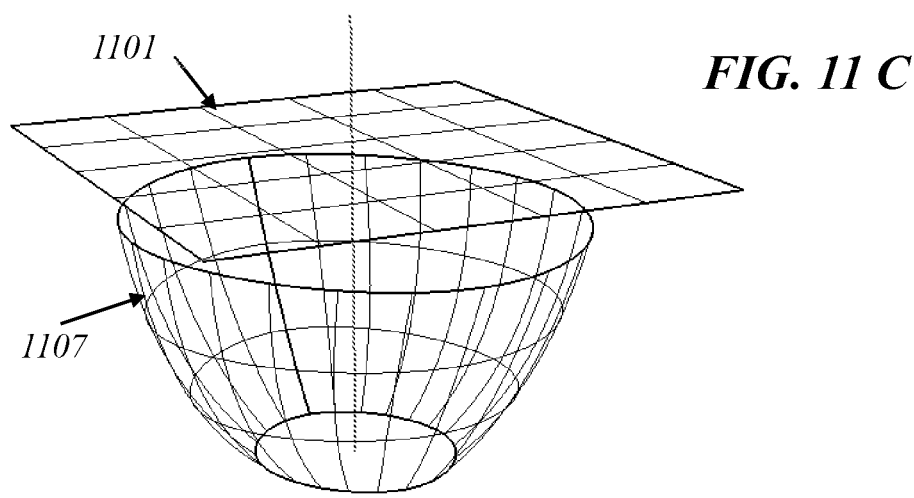

3. For large off-axis angles or for a more complex off-axis or non rotationally symmetrical radiation pattern, a new back surface can be derived. FIGS. 11A, 11B, and 11C, collectively FIG. 11, show the 3D wavefront method to calculate a freeform back surface. In FIG. 11A, a source 1104 and a cavity, consisting of cylinder 1103 and cavity lens 1102, are shown. Exit surface 1101 is a flat surface. The back surface is derived as follows. An outgoing wavefront 1105 (FIG. 11B) is chosen that contains the information of what off-axis radiation pattern is to be obtained. The outgoing wavefront is in this case a cylindrical surface, although any other suitably well-behaved wavefront with or without any symmetry can be used. However it must be possible to propagate the wavefront free of caustics throughout the space in which the back surface is being created. A centered cylindrical wavefront 1105 would provide an extended oval beam pattern, centered at the source axis. The outgoing wavefront must be traced back through the exit surface. The source wavefront, in the point source approximation, is a spherical wavefront that, when propagated and refracted at the cavity, becomes an aspheric rotationally symmetric surface 1106. A generalized Cartesian surface that couples wavefronts 1105 and 1106 can be numerically calculated and is shown as freeform surface 1107 (FIG. 11C), which will be the back reflecting surface for the photon funnel (cavity and lens are not shown in FIG. 11C for simplicity).

Although specific embodiments have been described, the person skilled in the art will understand how features of different embodiments may be combined, and how features may be substituted or modified, without departing from the scope of the claimed invention.

For example, although the reflectors 206, 207, 406, 407, 506, 507, 602 have each been described as a single rotationally symmetrical surface, any of them may be designed by any of the methods described with reference to any of FIGS. 9, FIG. 11A, FIG. 11B and FIG. 11C, and may therefore be two (or more) surfaces separated by an axial cut line, as in FIG. 10, or an asymmetrical surface as shown in FIG. 11A, FIG. 11B, or FIG. 11C.

For example, although a light source consisting of one or more LEDs in a plane has been described, other forms of light source, including light sources hereafter to be invented or developed, may be used. However, if the light source is not Lambertian, the shape of the lens and the reflecting back surface for a given beam pattern may be different. In the interests of simplicity, the LED has been approximated to a point source. Those skilled in the art will understand how a light source of non-negligible size will affect the shapes of the lens and reflector, and may limit the attainable precision of the beam pattern.

For example, although in all the embodiments the lens 202, etc. is a single optical surface producing a single beam, the lens may, like the reflector 602, 613 or 1001, 1002, be divided into two or more sections producing distinct beams.

The preceding description of the presently contemplated best mode of practicing the invention is not to be taken in a limiting sense, but is made merely for the purpose of describing the general principles of the invention. The full scope of the invention should be determined with reference to the Claims.

We claim:

1. A collimator comprising a transparent body having:
   a central axis;
   a central cavity bounded by a circumferential surface and a front lens surface, the lens surface shaped to refract light from a predetermined location on the central axis in the cavity through the body to and out through a front exit surface;
   an outer reflector surface shaped to reflect light from the predetermined location refracted by the circumferential surface of the cavity through the body to and out through the front exit surface;

wherein the reflector surface comprises first and second parts connected by an optically inactive surface, and at least one of said first and second parts is not symmetrical about the central axis;

wherein the circumferential surface, the front lens surface and the outer reflector surface are arranged to direct the light in at least two beams outside the front exit surface, one of said beams on said central axis and the other of said beams having a center diverging from said central axis; and wherein said optically inactive surface connects a radially outer end of the first part of the reflector surface to a radially inward end of the second part of the reflector surface, and wherein both first and second parts each form an angle greater than zero degrees with respect to the central axis.

2. A collimator according to claim 1, wherein:
said optically inactive surface is annular;
one of said first and second parts of said reflector surface is between the optically inactive surface and the front exit surface; and
the other of said first and second parts of said reflector surface is between the optically inactive surface and a rear end of the central cavity.

3. A collimator according to claim 1, wherein said first and second parts of the reflector surface are on different sides of said central axis and are not symmetrical with each other under rotation about said central axis, and said optically inactive surface extends rearwards from said front exit surface.

4. A collimator according to claim 1, wherein outside the front exit surface the beam diverging from said central axis is narrower than the on-axis beam.

5. A collimator according to claim 1, wherein outside the front exit surface the beam diverging from said central axis is wider than the on-axis beam.

6. A collimator according to claim 1 that provides an on-axis beam from the front lens surface.

7. A collimator according to claim 1 that provides outside the front exit surface a beam diverging from said central axis from the front lens surface.

8. A collimator according to claim 1 that provides outside the front exit surface a beam having a center parallel to the central axis from the other of the first and second parts of the reflector surface.

9. A collimator according to claim 1, wherein the reflector surface is totally internally reflecting for light from the predetermined location.

10. A collimator according to claim 1, further comprising a source of light at the predetermined location.

11. A collimator according to claim 10, wherein the source of light is Lambertian, and is coaxial with the central axis.

12. A collimator comprising a transparent body having:
a central axis;
a central cavity bounded by a circumferential surface and a front lens surface, the lens surface shaped to refract light from a predetermined location on the central axis in the cavity through the body to and out through a front exit surface;
an outer reflector surface shaped to reflect light from the predetermined location refracted by the circumferential surface of the cavity through the body to and out through the front exit surface;
wherein the reflector surface comprises first and second parts connected by an optically inactive surface, and at least one of said first and second parts is not symmetrical about the central axis;
wherein the circumferential surface, the front lens surface and the outer reflector surface are arranged to direct the light in at least two beams outside the front exit surface, one of said beams on said central axis and the other of said beams having a center diverging from said central axis;
wherein said first and second parts of the reflector surface are on different sides of said central axis and are not symmetrical with each other under rotation about said central axis, and said optically inactive surface extends rearwards from said front exit surface; and
wherein said optically inactive surface comprises optically inactive surface portions on opposite sides of the central axis, connecting respective edges of the first and second parts of the reflector surface.

\* \* \* \* \*